US010610257B2

(12) United States Patent
Hacker

(10) Patent No.: US 10,610,257 B2
(45) Date of Patent: Apr. 7, 2020

(54) STRUCTURAL ELEMENT WITH BAYONET HAVING A UNIVERSAL BLADE FITTING WITH ELECTRICAL SOURCE POD AND TERMINAL CONFIGURATION

(71) Applicant: Nano 2.0 Business Press, LLC, Delray Beach, FL (US)

(72) Inventor: Steven M. Hacker, Delray Beach, FL (US)

(73) Assignee: Nano 2.0 Business Press, LLC, Delray Beach, FL (US)

( * ) Notice: Subject to any disclaimer, the term of this patent is extended or adjusted under 35 U.S.C. 154(b) by 126 days.

(21) Appl. No.: 15/898,511

(22) Filed: Feb. 17, 2018

(65) Prior Publication Data

US 2020/0038049 A1   Feb. 6, 2020

(51) Int. Cl.
*B26B 5/00* (2006.01)
*A61B 17/3211* (2006.01)
*A61B 17/32* (2006.01)

(52) U.S. Cl.
CPC .... *A61B 17/3211* (2013.01); *A61B 17/32002* (2013.01); *A61B 2017/32113* (2013.01)

(58) Field of Classification Search
CPC .......... B26B 5/00; B26B 5/003; B26B 5/001; B26B 29/02; B26B 29/025; A22B 5/68; A61B 2017/32113; A61B 17/3213; A61B 17/3211; A61B 2090/034
USPC ... 30/329, 293, 162, 151, 26, 342, 340, 286, 30/335, 337; 132/200; 606/167, 170, 606/172, 180
See application file for complete search history.

(56) References Cited

U.S. PATENT DOCUMENTS

| 5,342,379 A * | 8/1994 | Volinsky ............ A61B 17/3213 30/162 |
| 5,423,843 A * | 6/1995 | Werner .............. A61B 17/3211 30/162 |
| 2008/0249550 A1* | 10/2008 | Djordjevic ......... A61B 17/3213 606/167 |
| 2010/0324577 A1 | 12/2010 | Dunn |

(Continued)

FOREIGN PATENT DOCUMENTS

WO    2014089369 A1    6/2014

OTHER PUBLICATIONS

International Search Report and Written Opinion, PCT Patent Appln. No. PCT/US2019/018374, ISA/US, dated Apr. 26, 2019.

*Primary Examiner* — Ghassem Alie
(74) *Attorney, Agent, or Firm* — Nancy J. Flint, Attorney at Law, P.A.; Nancy J. Flint, Esq.

(57) ABSTRACT

An assembly having a support element with a bayonet having a universal blade fitting inserted into the interior of a tube and an electrical source pod is disclosed. The tube is releasably attached to a handle and a blade is attached to the universal blade fitting to form a terminal configuration, such as a surgical scalpel. The support element provides stability and support for pressure placed on the blade to minimize or prevent breakage of the bayonet during cutting. The support element also provides a lever support and function for the tube it is attached to and the handle that attaches to it. Finally, the support element also serves as a guide rail for all assembly components to adhere to and along upon assembly of all components such as tube, electrical source pod and battery cartridge.

12 Claims, 10 Drawing Sheets

(56) References Cited

U.S. PATENT DOCUMENTS

| | | |
|---|---|---|
| 2013/0079804 A1* | 3/2013 | Milton .............. A61B 17/3213 606/167 |
| 2014/0182140 A1* | 7/2014 | Rosenhan .............. B26B 5/003 30/162 |
| 2015/0119650 A1 | 4/2015 | Hacker |
| 2015/0150579 A1 | 6/2015 | Hacker |
| 2016/0262825 A1 | 9/2016 | Jayaraj |
| 2018/0125524 A1 | 5/2018 | Levy |

* cited by examiner

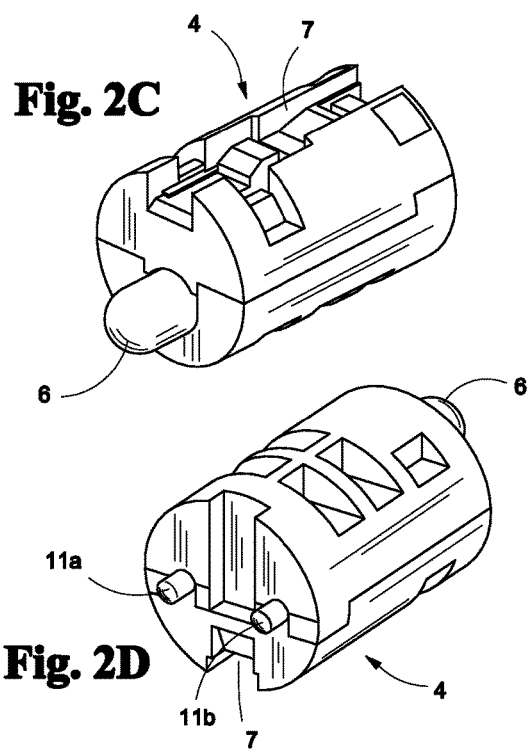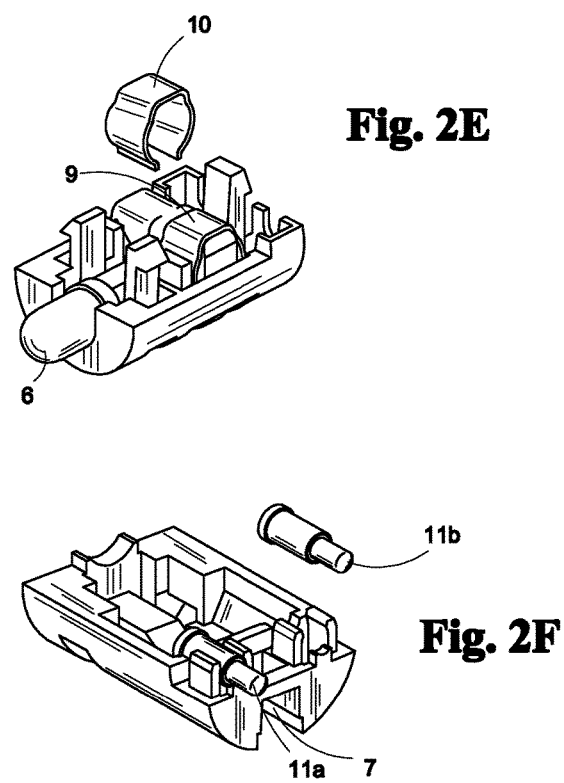

STRUCTURAL ELEMENT WITH BAYONET HAVING A UNIVERSAL BLADE FITTING WITH ELECTRICAL SOURCE POD AND TERMINAL CONFIGURATION

FIELD OF THE INVENTION

The invention relates to an assembly comprising a support element having a bayonet with a universal blade fitting housed in the interior of a tube. The assembly can further comprise an electrical source pod. The assembly is releasably attached to a handle and a blade to form a terminal configuration, such as a surgical scalpel.

BACKGROUND OF THE INVENTION

Physicians and surgeons use a handle to attach to a blade to cut human tissue for a variety of purposes.

Finding the right shape, size and material handle, as well as illumination options varies by surgeon's preference and cost and space on tray. Surgeons will often have multiple scalpels on one tray.

In the art, many shapes and materials are used for handles that have a variety of shapes and sizes, for example plastic, steel and aluminum. Some handles further provide an illumination.

U.S. Pat. No. 8,690,872 discloses surgical pencils that visualize a surgical site. The surgical pencils comprise a removable lighting device that is attached inside an electro cautery handle.

U.S. Pat. No. 9,072,541 discloses a surgical scalpel handle with an attached LED cartridge that is attached externally via reverse threads to an externally configured and central axis oriented strut on the exterior of a scalpel handle.

Additional prior art can be seen in U.S. Pat. Nos. 7,172,611; 8,181,352; 8,291,601; U.S. Design Pat. No. D704337; U.S. Pat. Nos. 8,409,231; and 8,409,232.

Significant cost and resources are necessary for a surgeon to have many different types of handles as well as the space limitations on a surgical tray.

Further, most universal bayonet blade fittings are molded as a single part as an extension with the handle or permanently affixed to the handle and the use of different handle shape and sizes requires using multiple handles and there is no structural support strut to prevent the universal bayonet fitting from breaking off during surgery.

BRIEF SUMMARY OF THE INVENTION

In one embodiment of the invention, an assembly is disclosed comprising a support element having a bayonet with a universal blade fitting housed in the interior of a tube, wherein the assembly is releasably attached to a handle that can be manufactured in any shape and from any material to form a terminal configuration such as a surgical scalpel.

In one embodiment, the assembly further comprises a non-disposable reusable sterilizable electrical source pod.

In one embodiment, the assembly further comprises a disposable electrical source pod.

In one embodiment, the support element comprises a non-disposable reusable material of manufacture.

In one embodiment, the support element comprises a disposable non-reusable material of manufacture.

In one embodiment, the assembly comprising the support element, bayonet with universal blade fitting and electrical source pod assembly are releasably inserted into the tube, and the handle is releasably attached to one end of the tube.

In one embodiment, a removable battery cartridge is attached to the assembly within the tube.

In one embodiment, a single board computer (SBC) with or without Wi-Fi® and Bluetooth® wireless connectivity technology, or a removable computer or electronic circuitry device comprising a resistor, a printed circuit board, Bluetooth® wireless connectivity technology, miniature video camera, location-based software and/or a computing microchip are attached to the assembly within the tube.

In one embodiment, a variety of cutting blades can be attached to the bayonet with universal blade fitting to form a terminal configuration. In one embodiment, the blade is a scalpel blade and the terminal configuration is a surgical scalpel.

BRIEF DESCRIPTION OF THE DRAWINGS

The various features of the present invention and the manner of attaining them will be described in greater detail with reference to the following description, claims, drawings, wherein reference numerals are reused, where appropriate to indicate a correspondence between the referenced items, and wherein the preferred embodiments of the invention will herein after be described in conjunction with appended drawings to illustrate and not to limit the invention wherein like designations denote like elements and in which:

FIGS. 2C to 2F depict assembled and cut-away views of an electrical source pod in accordance with one embodiment of the invention;

DETAILED DESCRIPTION OF THE PREFERRED EMBODIMENT

Figure 1:
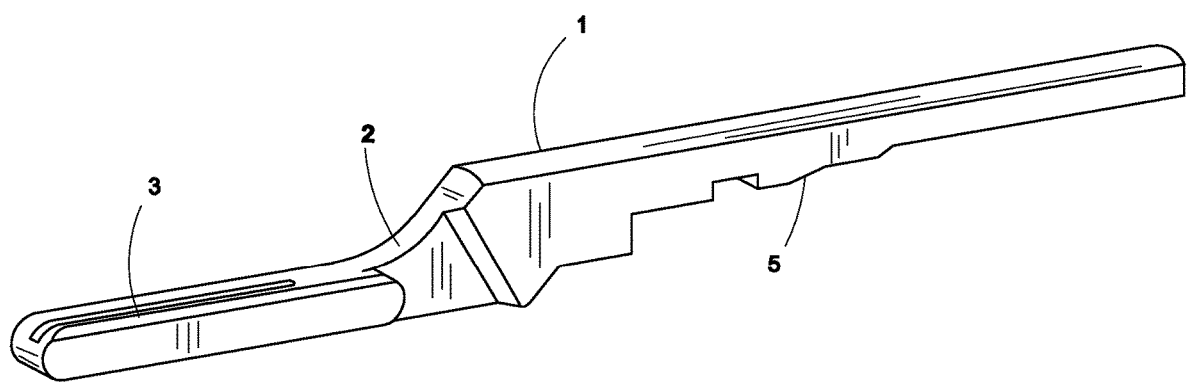
FIG. 1 depicts a side view of a support element with a bayonet having a universal blade fitting in accordance with one embodiment of the invention.

The invention relates to an assembly comprising a support element with a bayonet having a universal blade fitting inserted into the interior of a tube and optionally including an electrical source pod. One or both of the bayonet and electrical source pod are releasably attached to the support element in one embodiment of the invention. The assembly is inserted into the tube, and a handle is attached to one end of the tube to form a terminal configuration. The handle may comprise any shape and size and may be manufactured from any material. A blade is releasably attached to the universal blade fitting of the bayonet. The blade may comprise any type of blade as desired by the user. The terminal configuration comprises any type of terminal configuration, for example box cutters or medical devices. In one embodiment, the terminal configuration is a surgical scalpel and the blade is a surgical scalpel blade. The support element provides stability and support for pressure placed on the blade to minimize or prevent breakage of the bayonet during cutting. The support element also provides a lever support and function for the tube it is attached to and the handle that attaches to it. Finally, the support element also serves as a guide rail for all assembly components to adhere to and along upon assembly of all components such as tube, electrical source pod and battery cartridge.

In one embodiment, one or more of the various elements are manufactured from a reusable material.

In one embodiment, one or more of the various elements are manufactured from a disposable material.

In one embodiment, the assembly comprising the structural element with a bayonet having a universal blade fitting and electrical source pod are releasably inserted into a tube, and the handle is releasably attached to one end of the tube.

In one embodiment, the assembly comprising the structural element with a bayonet having a universal blade fitting and optionally an electrical source pod are welded or glued to the tube, and the handle is releasably attached to one end of the tube.

In one embodiment, a removable battery cartridge is attached to the assembly within the tube.

In one embodiment, both the removable battery cartridge and the Electrical source pod use the support element as a locating key and guide rail for insertion into the terminal configuration.

In one embodiment, the electrical source pod comprises an LED bulb with or without a resistor, and with or without a printed circuit board. The printed circuit board connects and supports electrical components. The resistor controls the flow of current through the circuit. In one embodiment, the electrical source pod comprises a plurality of LED bulbs with or without a resistor, and with or without a printed circuit board.

In one embodiment, a variety of cutting blades can be attached to the universal blade fitting on the bayonet to form a terminal configuration. In one embodiment, the blade is a scalpel blade and the terminal configuration is a surgical scalpel.

In one embodiment, a single board computer (SBC) with or without Wi-Fi® and Bluetooth® wireless connectivity technology, or a removable computer or electronic circuitry device comprising a resistor with or without a printed circuit board, or a printed circuit board with or without a resistor, Bluetooth® wireless connectivity technology, miniature video camera, location-based software and/or a computing microchip are contained within the electrical source pod and attached to the assembly within the tube. The computer and video functionality allow for interfacing with electronic health records, and can also digitally record and document the activity of the handle, the type of surgery, the location of surgery, the pattern of cutting, the type of surgery performed, the patient identity and the surgeon identity, can video record the surgery, and can record that verification steps taken prior to surgery properly confirm correct patient, surgery type, location.

FIG. 1 depicts a side view of a support element 1 having a bayonet with a universal blade fitting in accordance with one embodiment of the invention. Support element 1 and bayonet with universal blade fitting 3 comprise a single unit and are in longitudinal coordination, wherein proximal end of bayonet with universal blade fitting 3 is disposed at distal end of support element 1. Support element 1 and bayonet with universal blade fitting 3 comprise a tab 2 and a stepped profile on the undersurface in longitudinal coordination with the length of the support element 1. A pair of guiderails 5 are disposed on the sides and undersurface of support element 1.

Figure 2A:
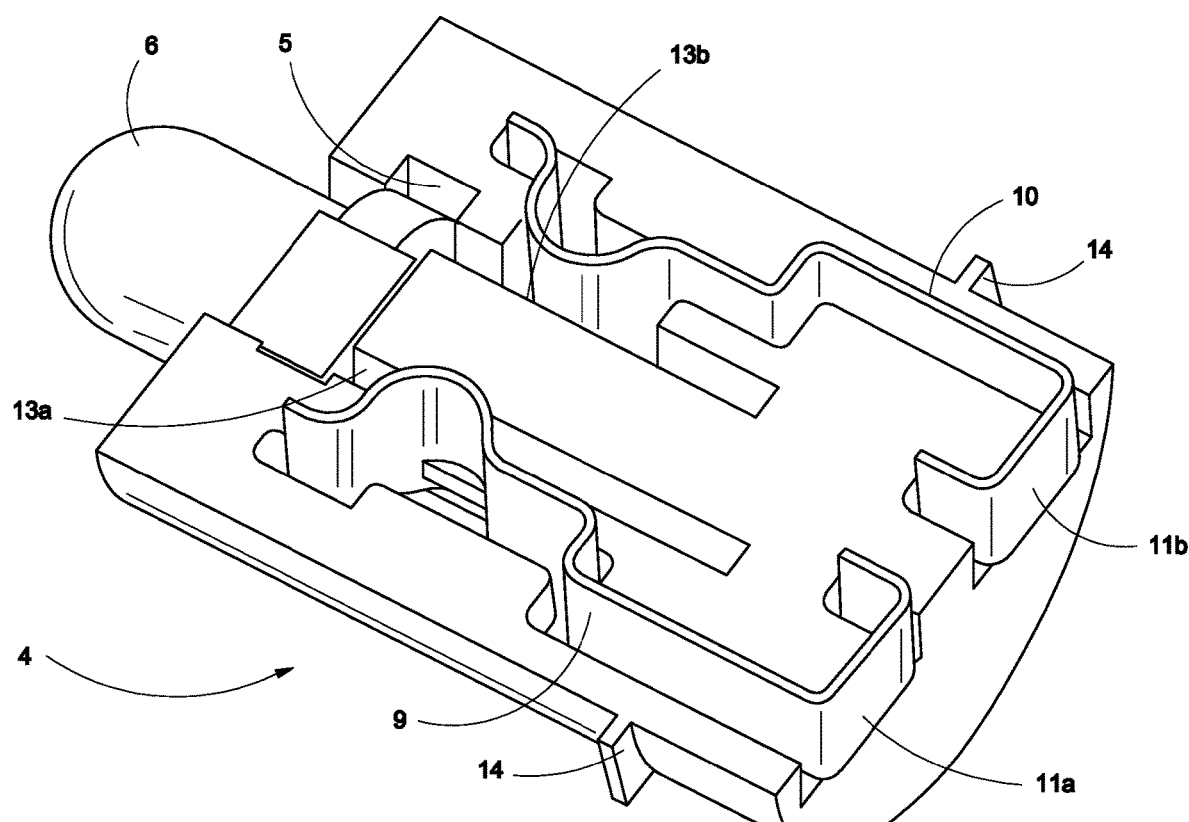
FIG. 2A depicts a cut-away view of the interior components of an electrical source pod in accordance with one embodiment of the invention.

FIG. 2A depicts a cut-away view of the interior components of an electrical source pod 4 in accordance with one embodiment of the invention. The interior of electrical source pod 4 comprises a light bulb 6 disposed on the distal end of electrical source pod 4.

The interior of electrical source pod 4 further comprises a positive electrical lead 13a and a negative electrical lead 13b in electrical communication with light bulb 6. A positive contact 9 and a negative contact 10 form electrical contact with correspondingly charged electrical leads 13a and 13b. Positive contact 9 terminates into a positive terminal 11a that extends to the exterior proximal end of electrical source pod 4 and negative contact 10 terminates into negative terminal 11b that extends to the exterior proximal end of electrical source pod 4. Electrical source pod 4 further comprises a plurality of tabs 14 disposed on the interior opposing sides of electrical source pod 4 to snap together the top and bottom halves of electrical source pod 4.

Figure 2B:
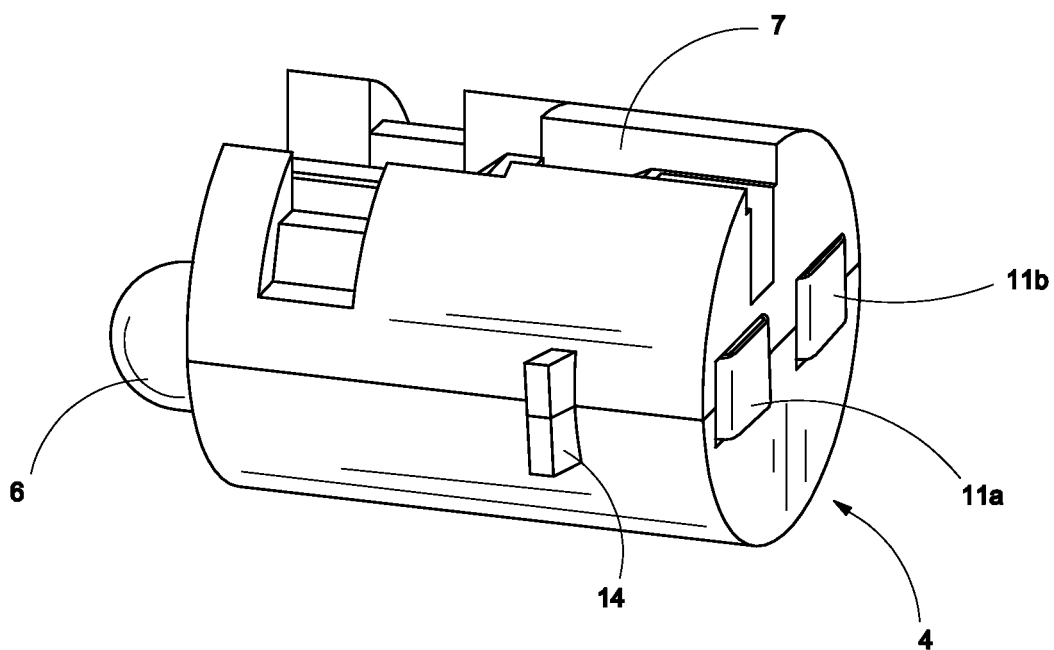
FIG. 2B depicts an assembled view of an electrical source pod in accordance with one embodiment of the invention.

FIG. 2B depicts an assembled view of electrical source pod 4 in accordance with one embodiment of the invention wherein light bulb 6 extends outwardly from distal end of electrical source pod 4 and positive and negative terminals 11a and 11b are shown on the exterior proximal end of assembled electrical source pod 4. Electrical source pod 4 comprises a key cutout 7 on its top surface for orientation and mating with the stepped profile on the bottom surface of support element 1 and guiderails 5. Key cutout 7 comprises a front flexible arm 8a and a rear arm 8b. The exterior of electrical source pod 4 further comprises side tabs 14 on opposing sides.

FIGS. 2C to 2F depict an alternative electrical source pod 4 suitable for use in accordance with one embodiment of the invention wherein light bulb 6 extends outwardly from distal end of electrical source pod 4 and positive and negative terminals 11a and 11b are shown on the exterior proximal end of assembled electrical source pod 4. Electrical source pod 4 comprises a key cutout 7 on its top surface for orientation and mating with the stepped profile on the undersurface of support element 1 and guiderails 5. The exterior of electrical source pod 4 further comprises side tabs 14 on opposing sides. A positive contact 9 and a negative contact 10 form electrical contact with light bulb 6. In one embodiment, the contact comprises correspondingly charged terminals 11a and 11b. In this embodiment, positive terminal 23a and negative terminal 23b of electrical battery cartridge 16 as discussed with regard to FIG. 3A can be adapted accordingly to connect with positive terminal 11a and negative terminal 11b of electrical source pod 4 and lighting bulb 6.

Figure 3A:
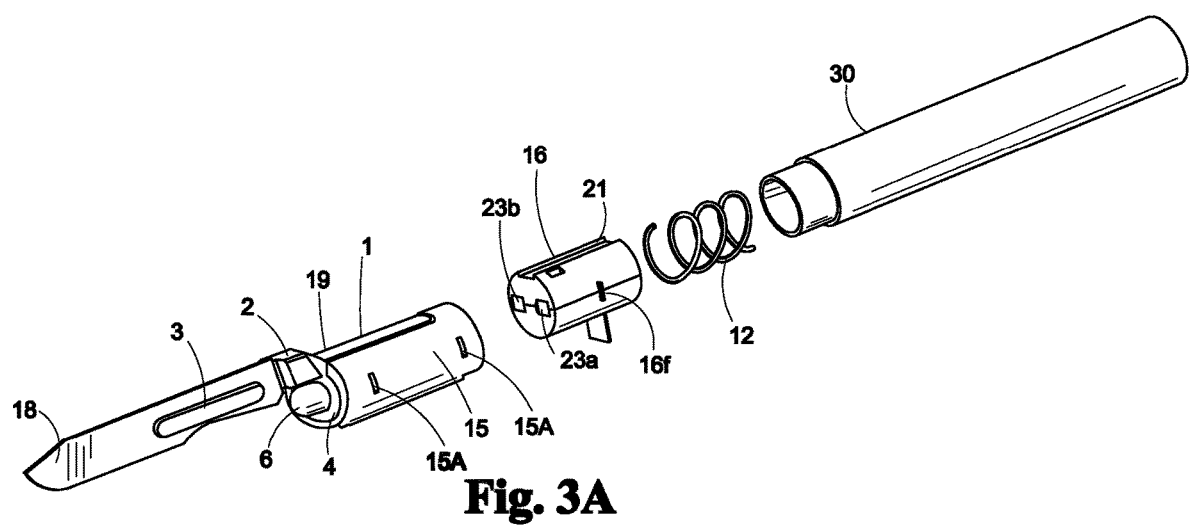
FIG. 3A depicts an exploded view of an assembly comprising a support element with bayonet having a universal blade fitting and an electrical source pod inserted into tube; a removable battery cartridge inserted into the tube; and a handle releasably attached to one end of the tube in accordance with one embodiment of the invention.

FIG. 3A depicts a side view of an assembly comprising a support element 1 having bayonet with a universal blade fitting 3 and an electrical source pod 4 inserted into tube 15 along groove 19 that mates with guide rails 5 on support element 1; a removable battery cartridge 16 with key cutout 21 for orientation and mating to support element 1 upon insertion into tube 15; electrical source pod 4 with key cutout 7 for orientation and mating with the stepped profile on the undersurface of support element 1 and guiderails 5 upon insertion into tube 15; and a handle 30 releasably attached to one end of tube 15 in accordance with one embodiment of the invention. A cutting blade 18 is attached to bayonet with a universal blade fitting 3. Distal end of tube 15 comprises a cutout groove 19 on the top surface that mates with guiderails 5 and support element 1 and releasably accommodates tab 2 and the stepped profile on the undersurface of support element 1 with bayonet having a universal blade fitting 3. Tube 15 further comprises a plurality of slits 15a that mate with tabs 14 of electrical source pod 4 when it is inserted into the interior of tube 15. In one embodiment, tube 15 and support element 1 having bayonet with a universal blade fitting 3 are releasably attached and both tube 15 and support element 1 having bayonet with a universal blade fitting 3 can be sterilized for use in medical applications.

Handle 30 may comprise a disposable material or it may comprise a reusable material. In one embodiment, handle 30 comprises a surgical scalpel handle. In one embodiment, handle 30 can be sterilized for use in medical applications.

Blade 18 may comprise any type of cutting blade desired by the user. In one embodiment, blade 18 comprises a surgical scalpel blade. As is customary in surgical procedures, blade 18 can be removed from support element 1 having bayonet with a universal blade fitting 3 and disposed of after single use in medical applications or reused in non-medical applications.

A spring 12 may be inserted in the interior cavity of handle 10 to exert pressure on battery cartridge 16 when handle 30 is attached to the proximal end of tube 5, thus creating an electrical connection with positive terminal 23a and negative terminal 23b of electrical battery cartridge 16 with positive terminal 11a and negative terminal 11b of electrical source pod 4 and lighting bulb 6.

Figure 3B:
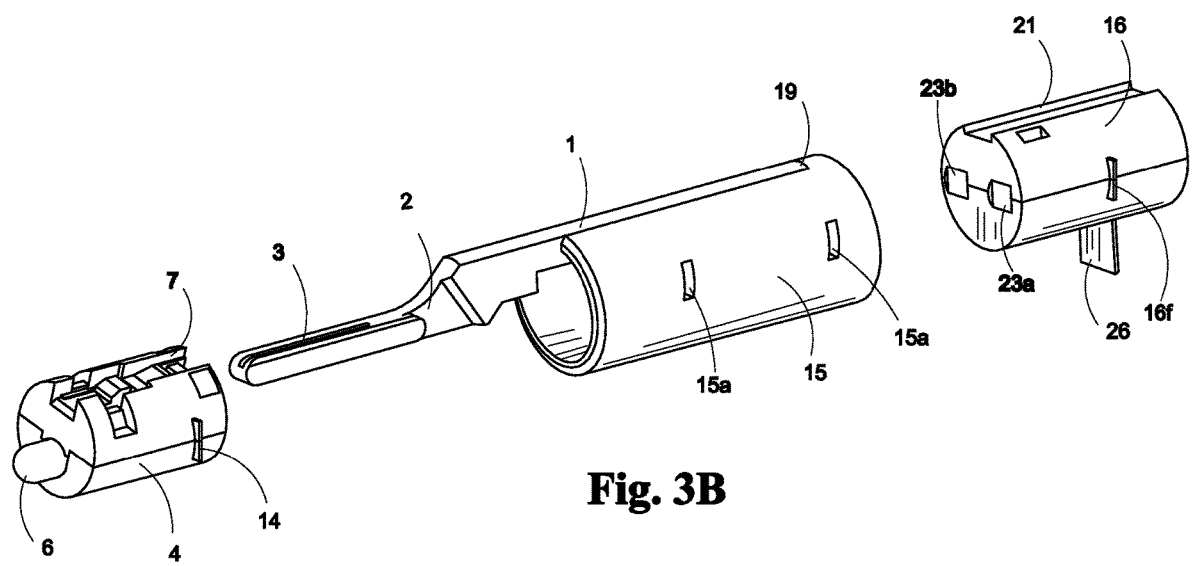
FIG. 3B depicts a component view of an assembly comprising a support element with bayonet having a universal blade fitting and an electrical source pod inserted into the tube; a removable battery cartridge inserted into the tube; and a handle releasably attached to one end of the tube in accordance with one embodiment of the invention.

FIG. 3B depicts a perspective view of support element 1 with bayonet having a universal blade fitting 3 and an electrical source pod 4; tube 15; and removable battery cartridge 16 in unassembled condition.

Figure 4A:
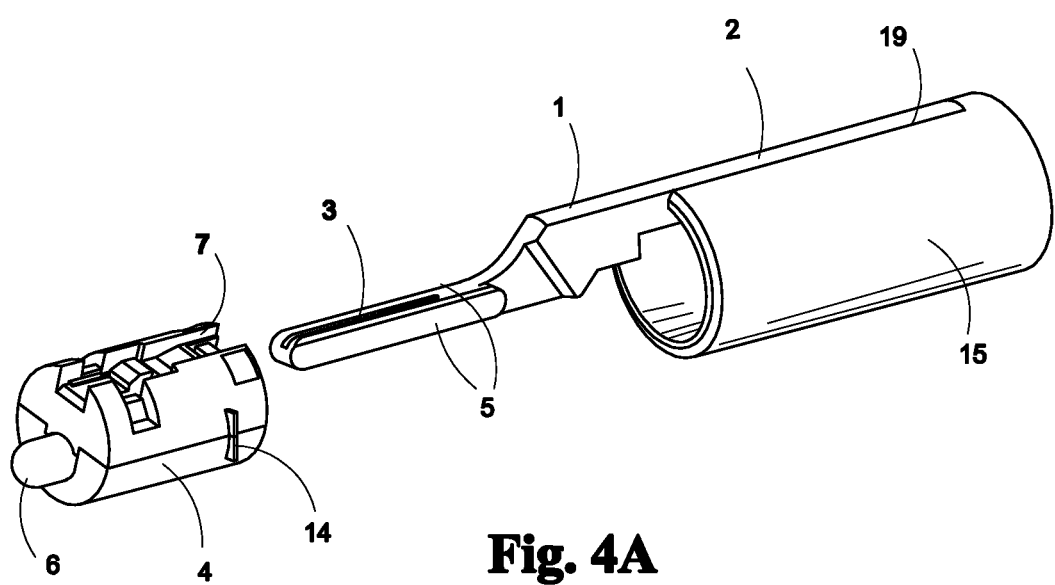
FIG. 4A depicts a perspective view of an assembly comprising a support element with a bayonet having a universal blade fitting and an electrical source pod in unassembled condition; and tube into which the assembly when assembled is inserted in accordance with one embodiment of the invention.

FIG. 4A depicts a perspective view of support element 1 having bayonet with a universal blade fitting 3; electrical source pod 4; and tube 15 in unassembled condition. Cutout groove 19 on the top surface of tube 15 mates with and releasably accommodates tab 2 and the stepped profile on the undersurface of support element 1 with bayonet having a universal blade fitting 3. Bulb 6 extends outwardly from distal end of tube 15. Guiderails 5 of support element 1 slide into key cutout 7 to securely attach support element 1 with tube 15. Tab 2 and of the stepped profile on the undersurface of support element 1 retain electrical source pod 4 in place and keep it from moving out of tube 15.

Figure 4B:
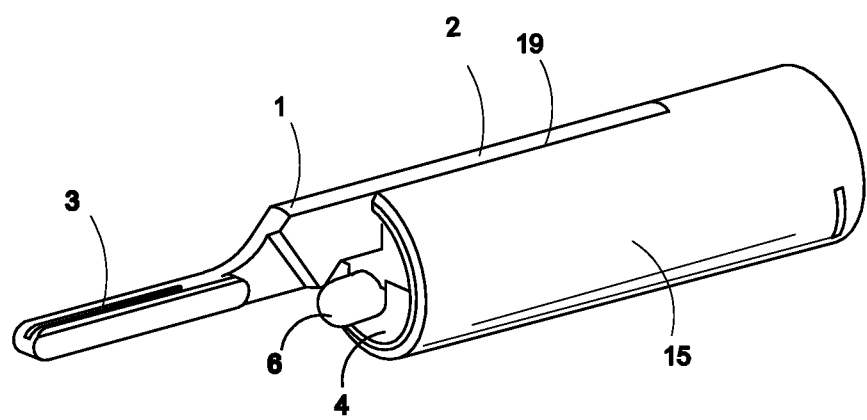
FIG. 4B depicts an assembly comprising a support element with a bayonet having a universal blade fitting and an electrical source pod in assembled condition as inserted into tube in accordance with one embodiment of the invention.

FIG. 4B depicts a perspective view of support element 1 having bayonet with a universal blade fitting 3; and electrical source pod 4 as inserted into the interior of tube 15. Cutout groove 19 on the top surface of tube 15 mates with and releasably accommodates guiderails 5 and tab 2 and the stepped profile on the undersurface of support element 1 with bayonet having a universal blade fitting 3. In one embodiment, cutout groove 19 further comprises grooves (not shown) in its opposing interior walls configured to receive insertion of support element 1. Bulb 6 extends outwardly from distal end of tube 15.

Figure 5:
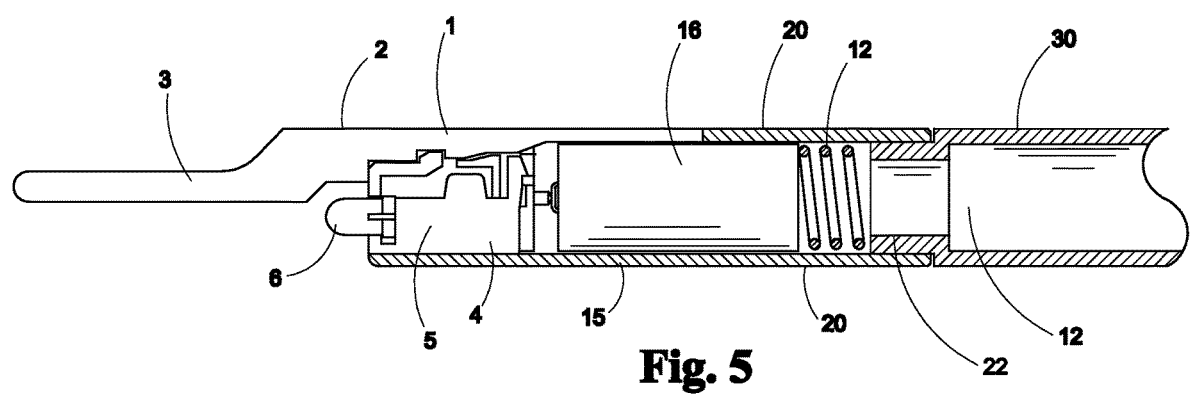
FIG. 5 depicts a side cut-away view of an assembly comprising a support element with a bayonet having a universal blade fitting and an electrical source pod inserted into tube; a removable battery cartridge inserted into the tube; and a handle attached to one end of the tube, in accordance with one embodiment of the invention.

FIG. 5 depicts a side cut-away view of an assembly comprising support element 1 having bayonet with a universal blade fitting 3; electrical source pod 4; and removable battery cartridge 16 inserted into the interior of tube 15. Handle 30 is attached to one end of tube 15 via a releasable attachment. Releasable attachment may comprise any coupling mechanism now known or later developed to attach two parts together. In one embodiment, releasable attachment means comprise flexible rear tabs 22 extending from the rear end of tube 15 distal from bayonet with universal blade fitting 3, wherein rear tabs 22 further comprise shoulders that mate with holes in one end of handle 30. Releasable attachment means could comprise threads on end of tube 15 that thread and mate with threads on end of handle 30. In other embodiments, releasable attachment means could comprise screw on threads; male/female mating of parts; twist on mechanism; snap on mechanism; or any other releasable attachment mechanism now known or later developed.

Figure 6C:
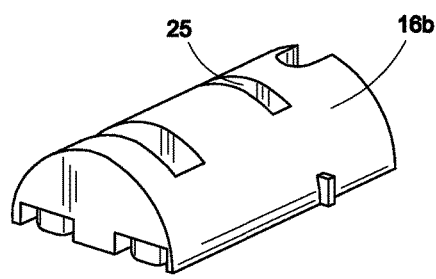
FIGS. 6A to 6C depict views of the removable battery cartridge.
Figure 6B:
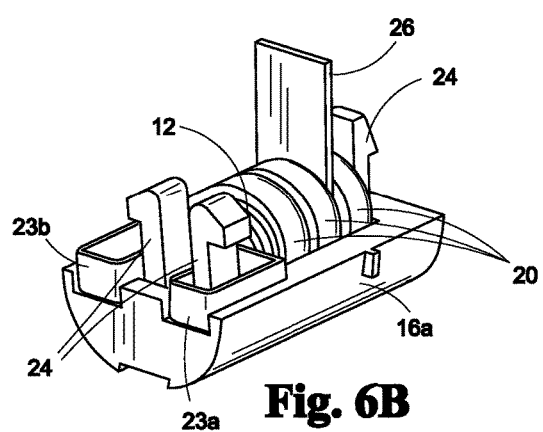
Figure 6A:
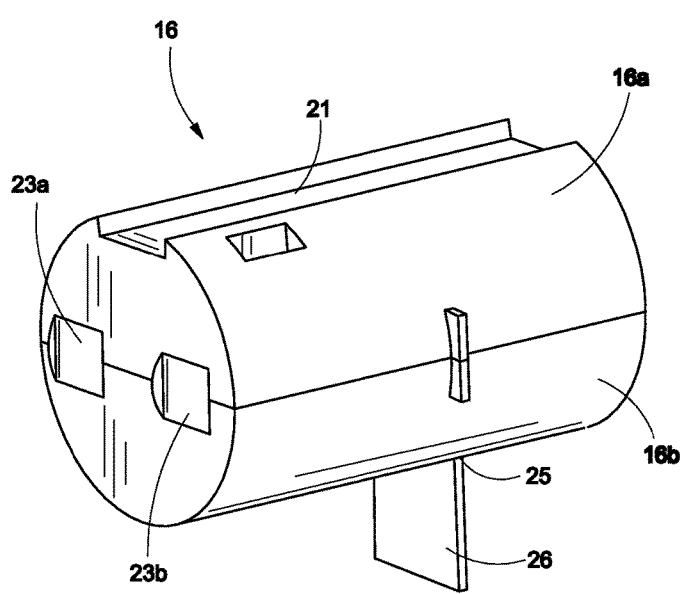

FIGS. 6A to 6C depict views of removable battery cartridge 16. Battery cartridge 16 has a bottom half 16b and a top half 16a, wherein the top half 16a comprises key cutout 21 and the bottom half 16b comprises a slit 25 through which paper tab 26 extends. Paper tab 26 is placed during assembly between at least two batteries 20 to serve as a circuit interruption and must be removed to complete an electrical circuit. In other embodiments not shown, any other type of circuit interrupter such as a switch may be used in place of the paper tab 26. Positive terminal 23a and negative terminal 23b are disposed on the proximal end of battery cartridge 16. One or more batteries 20 are stacked in a series in the interior of battery cartridge 16. Tabs 24 are disposed in the bottom of the interior cavity of battery cartridge 16 that engage together top and bottom halves 16a and 16b of battery cartridge 16. One or more springs 12 may be disposed in battery cartridge 16 to exert force to keep batteries 20 in stacked configuration and in electrical contact with each other. Batteries 20 may be disposable or rechargeable.

For an assembly comprising a surgical scalpel as the terminal configuration, after surgery is complete, blade 18 is removed and disposed of. Thereafter handle 30 and support element 1 with bayonet having universal blade fitting 3 and electrical source pod 4 are disassembled. Any or all terminal configuration parts that are made of a disposable material can be disposed of. If any or all terminal configuration parts that are made of non-disposable material, blade 18 is removed from the bayonet with universal blade fitting 3 and disposed of. Removable battery cartridge 16 is removed from the interior cavity of tube 15 and disposed of in its entirety if the batteries 20 are disposable. If the batteries 20 are rechargeable, they are removed and recharged. The parts that are made of non-disposable material may be properly sterilized prior to further use.

While this invention has been particularly shown and described with reference to certain embodiments, it should be understood by those skilled in the art that various changes in form and detail may be made therein without departing from the scope and spirit of the invention encompassed by the impended claims. The embodiments have been described in reference to an assembly comprising a support element attached to a bayonet having a universal blade fitting and an electrical source pod that is inserted into a tube, and a removable battery cartridge and a handle releasably attached to one end of the tube, and the principles apply to any terminal configuration or device, including a medical terminal configuration that is used on or in the body for treating, excising, incising or diagnosing including but not limited to skin hooks, dental mirrors, retractors, elevators, probes, curettes, and other instruments and that contains an handle. In certain embodiments, an electrical source pod may be omitted. Numerous modifications, changes, variations, substitution and equivalents will be apparent to those skilled in the art without departing from the spirit and scope of the invention as described in the claims.

What is claimed as new and desired to be protected by Letters Patent of the United States is:

1. A terminal configuration, comprising:
   a support element and a bayonet having a universal blade fitting attached to a distal end of the support element, wherein the support element and the bayonet having a universal blade fitting are in longitudinal coordination, wherein the support element has a top surface, a right side, a left side, and a bottom surface, wherein the support element and bayonet having a universal blade fitting comprise a single unit;
   a tab element disposed on the top surface of the support element and bayonet having a universal blade fitting;
   a guiderail element on the bottom surface of the support element;
   a tube, the tube comprising a first interior cavity, a proximal end, a distal end and a groove in the distal top surface of the tube;
   a electrical source pod;
   a removable battery cartridge;
   a handle;
   a blade,
   an electrical source pod comprising a second interior cavity, wherein the electrical source pod comprises a bulb, electrical contacts, resistors, printed circuit board, a positive terminal, a negative terminal, and the removable battery cartridge that are disposed within the interior cavity of the electrical source pod, wherein the positive terminal and negative terminal are in electrical connection with the bulb,
   wherein the electrical source pod has a bottom half and the top half that each have tabs that snap together and comprises a key cutout for orientation and mating upon insertion into the groove on the distal top surface of the tube,
   wherein the electrical source pod is releasably inserted into the first interior cavity of the tube,
   wherein the support element with bayonet having a universal blade fitting is releasably inserted within the first interior cavity of the tube through the distal end of the tube,
   wherein the tab element of the support element mates with the groove on the proximal top surface of the tube,
   wherein the handle releasably attaches to the proximal end of the tube,
   wherein a blade is releasably attached to the bayonet having a universal blade fitting,
   wherein the removable battery cartridge is inserted into the first interior cavity of the tube at the proximal end, wherein the removable battery cartridge electrically connects with the positive terminal and negative terminal disposed on the electrical source pod that are in electrical connection with the bulb.

2. The terminal configuration of claim 1, wherein the handle comprises a spring disposed in its interior that, upon mating with the tube, the spring exerts pressure on the removable battery cartridge to maintain electrical connection of the removable battery cartridge with the positive terminal and negative terminal of the electrical source pod.

3. The terminal configuration of claim 2, wherein the bulb comprises an LED bulb.

4. The terminal configuration of claim 1, wherein the blade comprises a surgical scalpel blade.

5. The terminal configuration of claim 1, wherein the handle and support element with the bayonet having a universal blade fitting are disposable.

6. The terminal configuration of claim 1, wherein the handle and support element with the bayonet having a universal blade fitting are reusable.

7. The terminal configuration of claim 6, wherein the handle and support element with the bayonet having a universal blade fitting are sterilizable.

8. The terminal configuration of claim 1, wherein the second interior cavity may be sealed such that the electrical source pod may be sterilized.

9. The terminal configuration of claim 1, wherein a single board computer (SBC) is inserted within the first interior cavity of the tube.

10. The terminal configuration of claim 9, wherein the single board computer (SBC) comprises wireless communication.

11. The terminal configuration of claim 9, wherein a miniature video camera is inserted within the first interior cavity of the tube.

12. The terminal configuration of claim 11, wherein the single board computer (SBC) comprises wireless communication.

* * * * *